United States Patent [19]

Martin, Jr.

[11] Patent Number: 5,470,560
[45] Date of Patent: Nov. 28, 1995

[54] METHOD FOR EVALUATING IMMUNOGENICITY

[75] Inventor: David W. Martin, Jr., San Francisco, Calif.

[73] Assignee: Genentech, Inc., South San Francisco, Calif.

[21] Appl. No.: 192,316

[22] Filed: Feb. 4, 1994

Related U.S. Application Data

[63] Continuation of Ser. No. 947,890, Sep. 18, 1992, abandoned, which is a continuation of Ser. No. 692,806, Apr. 25, 1991, abandoned, which is a continuation of Ser. No. 4,988, Jan. 20, 1987, abandoned.

[51] Int. Cl.$^6$ .......................... A61K 49/00; A61K 39/00; C12N 15/00
[52] U.S. Cl. .......................... 424/9.2; 424/184.1; 424/9.1; 435/7.1; 800/2; 800/DIG. 1; 935/111
[58] Field of Search ........................ 424/9, 184.1; 800/2, 800/DIG. 1; 435/7.1; 935/111

[56] References Cited

U.S. PATENT DOCUMENTS

| | | | |
|---|---|---|---|
| 4,396,601 | 8/1983 | Salser et al. | 424/93.21 |
| 4,736,866 | 4/1988 | Leder et al. | 800/2 |

OTHER PUBLICATIONS

Wilmut et al New Scientist 7:56–59 (1988).
Van Brunt Biotechnology 6(10):1149–1154 (1988).
Adams et al Nature 325 1987 223–228.
Adams, "Non–Tolerance and autoantibodies to a transgenic self antigen expressed in pancreatic β cells", Nature 325(6101):223 (1987).
Brinster et al., "Somatic Expression of Herpes Thymidine Kinase in Mice following injection of a Fusion Gene into Eggs", Cell 27:223–231 (1981).
Hammer et al., "Production of transgenic rabbits, sheep and pigs by microinjection", Nature 315:680–683 (1985).
Mullins et al., "Fulminant hypertension in transgenic rats harbouring the mouse Ren–2 gene", Nature 344:541–544 (1990).
Palmiter et al., "Dramatic growth of mice that develop from eggs microinjected with metallothionein–growth homone fusion genes", Nature 300:611–615 (1982).
Stewart, "Transgenic Mice as a Model to Test the Immunogenicity of Proteins Altered by Site–specific Mutagenesis", Mol. Biol. Med. 6:275–281 (1989).
Wilmut, "A revolution in animal breeding", New Scientist pp. 56–59 (1988).
Van Brunit, "Molecular Farming: Transgenic Animals as Bioreactors", Nature 6(10):1149, 1151–1152, 1154 (1988).
Palmiter et al., Nature, 300: 611–625 (1982).

Primary Examiner—Jasemine C. Chambers
Attorney, Agent, or Firm—Jeffrey S. Kubinec

[57] ABSTRACT

Biological effects of agents for diagnostic or therapeutic use are evaluated by administration of the agents to transgenic animals which are transformed with heterologous DNA and which are immune tolerant to the expression product of the heterologous DNA. In a further embodiment, preparations that are immunogenic in the transgenic animal model are purified by reverse immunoaffinity chromatography on antibody obtained from responding transgenic animals.

9 Claims, 5 Drawing Sheets

METHOD FOR EVALUATING IMMUNOGENICITY

This is a continuation of U.S. Ser. No. 07/947,890 filed Sep. 18, 1992, now abandoned, which is a continuation of U.S. Ser. No. 07/692,806 filed Apr., 25 1991, now abandoned which is a continuation of U.S. Ser. No. 07/004,988 filed Jan. 20, 1987, now abandoned.

This invention relates to methods for determining the biological activity of a substance in animals to which the substance is to be administered for therapeutic or diagnostic purposes. In particular it is concerned with methods for identifying immunogenic activity in preparations containing therapeutic recombinant polypeptides and eliminating the immunogenic components from such preparations.

The commercial development of substances having human in vivo therapeutic or diagnostic utility requires studies showing that the substances are safe. The pharmaceutical industry has attempted to make such determinations in advance of entering Phase I clinical trials with humans, typically by using a plethora of conventional investigational models, both in vitro and in lower animals.

Recombinant polypeptides intended for in vivo use present special challenges. It is useful to determine the immunogenic potential of a candidate polypeptide or the products of polypeptide purification procedures in advance of committing resources to their large scale manufacture and entry into Phase I trials. It is known, for example, that certain preparations of methionyl N-terminal human growth hormone (met-hGH) used in a lengthy course of therapy for the treatment of hypopituitary dwarfism are associated with the appearance of antibodies against met-hGH in the serum of patients. These antibodies are innocuous. However, such antibodies in other circumstances may not be so benign.

The immunogenic components in the met-hGH preparations responsible for eliciting hGH cross-reacting antibody remain the subject of speculation. Theoretical models attribute immunogenicity in these preparations to changes in the hGH molecule introduced during processing and/or purification of the molecule after its expression in recombinant cells, to the presence of an N-terminal methionyl residue not found in the native molecule, or to contamination by bacterial substances that are adjuvant-active.

Another challenge .posed by recombinant technology is to determine the safety of predetermined deletions, insertions or substitutions of target amino acid residues in any polypeptide whose sequence is known. These variants may find use, for example, as agonists or antagonists of the parental sequence. In the case of methionyl N-terminal polypeptide the inserted methionyl residue is an artifact of direct expression in recombinant cells. Whatever the reason for making amino acid sequence changes, they may render the variant immunogenic.

In summary, alterations in recombinant proteins may result from changes in conformational structure, amino acid deletions, additions or modifications, substitution of carbohydrate or lipid constituents, intentional or unintentional mutational changes in the protein, interspecies variation, or in vitro chemical modifications to the native protein. Any of these alterations can result in the production of antibodies in recipients if there is a structural change in the protein to which the immune system of the recipient is responsive. Whatever the basis for the generation of antibodies in animals receiving recombinant polypeptides, methods are needed for determining whether such products bear immunogenic potential.

Currently, no entirely reliable method for predicting immunogenicity of human recombinant polypeptides in humans is available in the preclinical phase of drug development. For example, it is now conventional to administer the preparations to non-human primates and, after a course of treatment, to assay the animal's serum for seroconversion to antibodies capable of binding the substance. These studies inevitably are flawed by the fact that the animals' response could as well be based on the foreign nature of the human polypeptide. Primate studies are extremely costly and, because the number of available animals is so limited, it is difficult to obtain a statistically meaningful sample. Furthermore, such assays do not disclose whether the substance itself, or its contaminants, were responsible for the seroconversion. For example, is the amino acid sequence variation responsible for immunogenicity, or was it contaminants in the preparation that possessed adjuvant activity? Conventional assays also fail to disclose whether improper manipulation of the polypeptide, leading for example to incorrect disulfide bonds, is responsible for the immunogenicity. Methods are needed for determining whether the primary amino acid sequence of a novel polypeptide will be immunogenic in animals, exclusive of immunogenicity induced by polypeptide denaturation or nonhomologous contaminants.

Even if a preparation is shown to be immunogenic by conventional assays no method is available for conveniently removing or eliminating the immunogenic components or characteristics. Immunoaffinity chromatography is conventional for purifying polypeptides, but these procedures have heretofore concentrated on developing antibodies to the substance of interest rather than the contaminants. It is theoretically possible to adsorb an antiserum raised against the entire preparation to remove antibodies specific for the desired product, thus rendering the antiserum specific only for contaminants, but this requires large quantities of product for the adsorption and the separation methods frequently leave behind antibody subpopulations that bind to isolated epitopes of the product. Further, the adsorption methods are inefficient and may be incomplete, in which case product will be adsorbed to the immunoaffinity resin and lost to recovery. It would be highly desirable to provide an immunoaffinity chromatography resin and method that would adsorb contaminants only, allowing the desired product to pass through the resin, because the conditions required to elute antibody-bound product often denatures the product and the elution may be incomplete under milder conditions. A method is needed for preparing antibodies that will bind only to the antigenic contaminants in a preparation, and not to the desired product present in the preparation.

Transgenic animals are now conventional staples of academic research. Such animals have been produced by transfecting germ cells, somatic cells, or embryos with heterologous DNA, suitably implanting the transfected cells and allowing the cells to mature into or stably integrate into adult animals containing the heterologous DNA. A reproducible percentage of such animals transcribe and express the heterologous DNA as protein which can be identified in tissues including blood or serum.

Suitable methods for making transgenic animals are described in U.S. Pat. No. 4,396,601 and Palmiter et al., Nature 300:611 (1982). Palmiter et al. suggest employing growth hormone transgenic animals as models for gigantism, as a means of correcting genetic disease, and as a method for producing valuable gene products. However, no practical utility for transgenic animals has been disclosed to exist in the field of preclinical testing or the preparation of reagents for protein purification.

SUMMARY OF THE INVENTION

The objects of this invention are accomplished by a process comprising (a) preparing a transgenic animal that is transformed with nucleic acid encoding a heterologous polypeptide and which is immunologically tolerant to the heterologous polypeptide, (b) contacting the animal with a preparation, (c) observing the animal for the development of a biological response to the preparation, (d) modifying the preparation and (e) repeating steps (b) and (c) to determine whether a change in the biological response has occurred as a result of the modification of the preparation. Specifically, if the biological response that is observed in step (c) is an immune biological response, then it is concluded that the test preparation will be immunogenic in nontransgenic homologous animals and the preparation is modified in an attempt to modify the immunogenicity as desired and the modified preparation reassayed in the transgenic system.

In a further embodiment of this invention, if the transgenic animal raises antibodies to a test preparation containing the heterologous polypeptide to which the animal is immunologically tolerant, then the test preparation is purified by contacting it with the antibody in order to bind the immunogenic components. Thereafter the antibody-bound, immunogenic components are removed from the preparation. This further embodiment is termed reverse affinity chromatography because it is the reverse of the conventional practice in which the desired substance is adsorbed to immunoaffinity resins.

DETAILED DESCRIPTION OF THE INVENTION

The transgenic or host animal preferably is a murine strain. Transgenic mice which have been seroconverted to preparation contaminants provide a convenient source of B-lymphocytes which express anti-contaminant antibodies. These are fused with myeloma lines or transformed with EBV in conventional fashion to produce a monoclonal antibody (or group of monoclonal antibodies) which binds to immunogenic substances in the test preparations. These antibodies then are used in the manufacture of a reverse immunoaffinity resin for purifying the preparation as is more fully described infra. However, it will be recognized that any other animal capable of raising an immune response will be satisfactory, e.g. pigs, goats, rabbits and rats. Here, the polyclonal antisera from transgenic seroconverted animals are useful in reverse immunoaffinity because they are available in larger quantity than from mice.

The selected host animals are rendered transgenic by transferring a nucleic acid encoding a heterologous polypeptide into early embryos of the intended host animal in accord with known practice. The nucleic acid is preferably DNA, but may be RNA where suitable retroviral vectors are available. The polypeptide is heterologous in that it encodes any polypeptide not found in animals of the strain which is to be transfected. The heterologous polypeptide preferably is a human polypeptide where the host animal is a non-human primate or other lower animal species.

The heterologous polypeptide is not limited to any particular class or source. Since the principal commercial utility for this invention is in the evaluation of preparations for administration to humans, the heterologous polypeptide generally will be human. Representative examples include hormones such as growth hormone, activin, relaxin, inhibin, prolactin release inhibitory factor, cytokines such as tumor necrosis factor, interferons, interleukins and suppressor factors, enzymes including tissue plasminogen activator, superoxide dismutase, enkephalinase and urokinase, clotting factors such as tissue factor and Factor VIII and other proteins such as serum albumin. The identity or function of the heterologous polypeptide is not critical.

The heterologous polypeptide ordinarily will be a secreted polypeptide, i.e., one which is found at one time or the other in the circulatory system, lymph nodes, extracellular fluid, cerebrospinal fluid or the like, but it also can be a cell membrane bound polypeptide. If the polypeptide to be assayed by the method herein is a predetermined variant, e.g. an amino acid sequence variant, a fusion or the product of postranslational covalent modification such as crosslinking, deglycosylation, or derivatization, then the DNA used to prepare the initial transgenic animal will encode the native protein as it would be found in vivo. If a preparation of an amino acid sequence variant is the subject of investigation, a dual transgenic study can be undertaken if necessary. The first set of transgenic animals are transformed with DNA encoding the native sequence, while another group is transformed with DNA encoding the variant sequence. The results using such animals will provide information about the immunogenicity of the variant per se as opposed to immunogenicity conferred by the post-translational handling, e.g., purification, of the variant under study.

The nucleic acid encoding the heterologous polypeptide preferably encodes the complete prepro and mature sequence of the selected polypeptide so that the mature polypeptide will be secreted into the circulatory system of the transgenic host. Alternatively, nucleic acid encoding the mature sequence will be ligated to a signal sequence recognized by the host animal. Suitable signal constructions can be evaluated readily by transfecting them into cell lines derived from the host species and the transformants assayed for secretion of the mature protein. Successful constructions then are used in transfections of germ or somatic cells in the preparation of the transgenic animals.

The nucleic acid encoding the heterologous polypeptide will also contain transcription and translational control sequences recognized by the host. Typically, these include promoters and enhancers to regulate transcription, and ribosomal binding domains to regulate translation. Ordinarily, when DNA encoding a human polypeptide is employed it is suitable to use the human transcriptional and translational control domains since they typically are recognized by other mammals. These need not be the control domains of the native gene encoding the heterologous polypeptide. Instead, control domains from other genes, e.g. insulin, are employed in order to confer tissue specificity of expression on the heterologous DNA in the host. However, it is within the scope herein to prepare hybrids comprising the transcriptional and translational control domains native to the host gene-homologous polypeptide ligated to DNA encoding the prepro human protein. Further, the genomic gene encoding the heterologous polypeptide is suitable, notwithstanding that it may contain introns. The introns and their location in the host-homologous gene also can be adapted to the heterologous polypeptide coding domains, as can the host's codon preference, including tissue preference codons if the appropriate tissue-specific control domains are used.

It is not necessary to use an inducible promoter to induce expression of the heterologous gene in the transgenic animals, nor is it necessary to include a selectable marker to facilitate selection of transformed host cells. Direct injection of the heterologous DNA into the host cell is preferred, particularly when the host is a fertilized egg. Direct injection is relatively efficient so that selection markers are not required. In fact, constitutive promoters are preferred since they will help to ensure that the transgenic animals express the heterologous gene during ontogeny so as to develop tolerance.

It is not necessary that the nucleic acid encoding the heterologous polypeptide and its control domains be transfected into the host cells in a plasmid or other replicable vector. However, the preparation of sufficient quantities of nucleic acid typically will require the use of a vector to clone the material unless it can be synthesized in vitro in adequate quantity.

Preferably, the host animal cell which is transformed with the DNA encoding the heterologous polypeptide will be an embryonic cell. This ensures that the mature animal which develops from the transfection will have had ample opportunity to express the heterologous polypeptide and, from an immunological standpoint, recognize it as "self", and so that the transfected gene is transmissible in the germ line. Embryonic cells, including fertilized eggs, are preferred because they are larger than spermatozoa and not motile. Somatic cells (in particular bone marrow cells) are acceptable so long as the transfection is undertaken before the development of the neonatal immune system in the host animal.

Animals that develop from transfections are screened for heterologous polypeptide in the serum or other body fluid. It is not critical that the polypeptide be present in elevated levels, or even at the levels of any endogenous homologue. The animal need only have produced sufficient polypeptide during the maturation of the immune system that it is rendered "tolerant" to the polypeptide, i.e. the transgenic animal is rendered incapable of raising antibodies to the polypeptide when the polypeptide preparation is administered to the transgenic animal under the intended therapeutic or diagnostic regimen. It is preferable to employ a bank of transgenic animals producing varying quantities of the heterologous polypeptide. Those producing the smallest amounts will be the most sensitive to the immunogenicity of fine changes made in the heterologous polypeptide. Animals that can only be determined to be transcribing the transfected DNA may be suitable; translation of polypeptide at levels below that which is detectable by immunoassay or functional tests for the heterologous polypeptide may be adequate to confer tolerance on the animal. Tolerance in the transgenic family model is determined by assaying serum samples from the intended transgenic host to determine upon challenge with the heterologous polypeptide whether the host is able to raise antibodies against the native heterologous polypeptide prior to administering the test preparation to other members of the transgenic animal family.

Transgenic animals that are tolerant to the heterologous polypeptide are contacted with the test preparation in any fashion calculated to induce an immune response. However, the heterologous polypeptide is preferably contacted with the host animal using the same route of administration, carriers and frequency of administration intended for the preparation in its in vivo therapeutic or diagnostic setting. If the dose, route and schedule of injection and buffer have not been established in patients, then these parameters can be derived from pre-clinical animal studies or from in vitro experiments. In the case of therapeutic proteins or polypeptides this may be by parenteral, intramuscular or subcutaneous administration in a pharmacologically-acceptable isotonic carrier such as saline, 5% dextrose, or phosphate buffer. Immunostimulants or adjuvants will not be included in the preparation, unless of course they are to be present in the preparation during its intended use. Multiples of the therapeutic or diagnostic dose also will be evaluated. Generally, the test preparation contains the heterologous polypeptide encoded by the transfected nucleic acid since it is the immunogenicity of this peptide that is to be determined. There are at least two embodiments, however, where the preparation will not contain the heterologous polypeptide.

In the first embodiment it may be desired to determine the immunogenicity of an amino acid sequence variant having such desired characteristics as antagonistic activity towards the native molecule, greater solubility or stability, resistance to enzyme digestion, improved biological half-life, and other features known to those skilled in the art. In this case the DNA used for transfection to generate the transgenic animal encodes the native primary amino acid sequence of the heterologous polypeptide, while the test preparation contains a heterologous polypeptide having a structure which is a variant of the native heterologous polypeptide.

In the second embodiment the preparation will contain a therapeutic or diagnostic agent that is expected to interact in vivo with the heterologous polypeptide encoded by the transfected DNA to produce an immunogenic or toxic response in the animal. For example, the heterologous polypeptide may encode an enzyme activity or cell surface receptor not normally found in the animal in question, but which is found in humans. There may be concern that a particular molecule will interact with the enzyme in humans to yield a product that might be toxic in vivo or combine with the receptor to exert an adverse effect on a host cell. While it is accepted practice to simply conduct preclinical studies on the product or the molecule in animals and postulate a homologous response to humans, more relevant information might be obtained by following the effect of in vivo generation of the product metabolite or receptor binding in what in essence is a transgenic analogue of the human enzyme or receptor system.

The immunogenicity of the test preparation optionally is compared to the immunogenicity of the native and denatured forms of proteins present in the preparation. These forms of the protein are negative and positive controls, respectively. The protein can be denatured for the positive controls by various procedures known to those skilled in the art, such as heating at 100° C. for 1–2 minutes or treatment with denaturing agents such as sodium dodecyl sulfate, 7M guanidine chloride or 8M urea. The positive control will establish whether the transgenic animals have the immune repertoire to respond to the protein treated to ensure that it is conformationally non-native. An additional immunogenicity positive control can be performed by combining the native test protein with an adjuvant to enhance the immune response in the transgenic host. Another positive control is to use the polypeptide from a third source e.g. bovine growth hormone, chinese hamster tPA or pig Factor VIII. The adjuvant can be any that are known to enhance the immunogenicity of the test protein in particular, or that are generally used to enhance the immunogenicity of proteins. Two commonly used techniques are to emulsify the protein in aqueous buffer with an equal volume of Freund's complete (FA) (for the first injection) or incomplete adjuvant (for later injections) or to co-precipitate the protein from solution using alum (Mishell, B. B. and Shiigi, S. M. (1980) in

*Selected Methods in Cellular Immunology*, Mishell, B. B. and Shiigi, S. M., eds., Appendix F, W. H. Freeman and Co., San Francisco, Calif.). The mixture of adjuvant and protein is then injected subcutaneously or intramuscularly into the transgenic animals. Although the injection schedule can be varied, two injections at 2 week intervals would be commonly used to test the immunogenicity of a protein. The doses tested would be 1, 3, 10, 30, 100, 300, 1000 µg per injection. Table 1 illustrates the experimental design for this additional immunogenicity test as it would be used with met-hGH.

TABLE 1

Immunogenicity Test of met-hGH with Adjuvant

| Number of Animals per Group | Dose | Adjuvant | Injection Schedule (wks) | Route of Injection | Bleeding Schedule (wks) |
|---|---|---|---|---|---|
| 6 | 1 µg | FA[a] | 0, 2 | i.p.[b] | 0, 4, 6 |
| 6 | 3 µg | FA | 0, 2 | i.p. | 0, 4, 6 |
| 6 | 10 µg | FA | 0, 2 | i.p. | 0, 4, 6 |
| 6 | 30 µg | FA | 0, 2 | i.p. | 0, 4, 6 |
| 6 | 100 µg | FA | 0, 2 | i.p. | 0, 4, 6 |
| 6 | 300 µg | FA | 0, 2 | i.p. | 0, 4, 6 |
| 6 | 1000 µg | FA | 0, 2 | i.p. | 0, 4, 6 |

[a]Freund's adjuvant
[b]intraperitoneal injection

Once the transgenic animal has been contacted with the test preparation it is observed for an adverse biological response. Such responses include birth defects, neoplasms, growth retardation, inflammation, tissue necrosis, and the like. When the response being observed is immunogenicity, serum samples from the animal are evaluated for the presence of antibodies against the test preparation, using as controls serum from the animal before contact with the test preparation and serum from mock-transgenic animals from the same strain which were contacted with the preparation under the same protocol as the transgenic animals. Serum samples are screened using conventional assays such as radioimmunoassays or ELISA systems.

Once it has been determined that the intended therapeutic or diagnostic preparation produces an observed effect in the transgenic animal steps are taken to modify the preparation so that it will not cause the same effect upon retesting in the transgenic hosts (in the case of undesirable effects) or will enhance the effect upon retesting (where desirable results are obtained). Obviously, the steps that will be taken depend upon the nature of the preparation and its therapeutic or diagnostic objective. If the preparation is immunogenic and contains a polypeptide that is intended to be as close as possible to the native form of the polypeptide from the standpoint of primary sequence, secondary and tertiary conformation and biological activity, then modifications will be made in the purification method used in making the preparation in order to reduce potential denaturing conditions, introduce procedures to purify away any adjuvant-active contaminants (as described below in the discussion on reverse immunoaffinity chromatography) and/or change the preparation formulation to introduce stabilizers for the polypeptide.

If the test preparation contained a predetermined amino acid sequence variation or in vitro covalent modification which proved to be biologically adverse then changes are made to reduce the effect. For example, if the preparation contained a primary amino acid sequence variant of a therapeutic polypeptide in which an amino acid residue had been substituted by another residue then the immunogenicity of the variant might be reduced by choosing another substituent. On the other hand, if the therapeutic purpose of the variant is to induce an immunogenic effect, e.g. the generation of neutralizing antibodies against the native heterologous polypeptide, then immunogenicity will be modified by enhancing the foreign character of the preparation.

Test preparations may contain polypeptides which have been derivatized by in vitro covalent modification, e.g. by the attachment of toxic substituents or radiopaque dyes to antibodies specific for tumor cell surface antigens or by the removal or addition of glycosyl residues. These may prove to be immunogenic in the transgenic model. If so, their methods for preparation or the nature of the substituent is changed in a fashion expected to reduce immunogenicity, for example by selecting another crosslinking or glycosylation site.

Small molecule, non-peptidyl drugs will be modified by alteration of substituent groups in the same fashion as is done today in studies using conventional animal toxicity models, either to reduce adverse side-effects or improve therapeutic or diagnostic efficacy.

The modified preparation then is subjected to the transgenic model anew in order to determine if the modifications have improved the characteristics of the preparation. Obviously, for immunogenicity studies a naive transgenic animal (one that has not been exposed to the first preparation) will be used with the modified preparation.

It is not within the scope of this invention to ensure that such modifications in fact will be successful in modifying biological effects nor, with the exception of reverse immunoaffinity, are the particular modifications within the scope hereof: the principal purpose of this invention is to inform as to whether the modifications made were in fact successful, not how to make them.

In the preferred embodiment referred to above as reverse immunoaffinity chromatography, the spleens of mice that develop antibodies to the preparation are harvested and employed to make hybridomas which produce antibodies against the immunogenic components in the test preparation. In essence, the hybridomas are not produced to identify a particular antibody-producing clone but rather to simply produce enough of the antibody for commercial use in reverse immunoaffinity purification. Alternatively, a large transgenic animal such as a goat need only be bleed from time to time and serum harvested for use in the manufacture of immunoaffinity columns. The principal advantage of immunoaffinity purifications using the antibody pool obtained from transgenic animals is that the desired immunologically-refractory substance in the preparation is not bound to the immobilized antibody but rather passes through the affinity resin. This obviates the need to elute the desired material from the antibody bound state, a procedure that often leads to considerable losses in activity and denaturation of the desired polypeptide. The antibodies for use in the reverse immunoaffinity resin are immobilized by conventional methods well known per se, e.g. by cross-linking to cyanogen bromide activated Sepharose.

The invention will be more fully understood in the light of the following examples, which should not be construed as limiting the invention.

EXAMPLE 1

Construction of Transfected Genes

DNAs encoding secreted mature human Factor VIII, tissue plasminogen activator (tPA) or growth hormone (hGH) were placed under the control of the mouse mammary tumor virus (MTV) promoter (MTV-hGH) or variants thereof, or the SV40 early promoter. The DNA constructions were made as follows:

1. hGH

Figure 1:
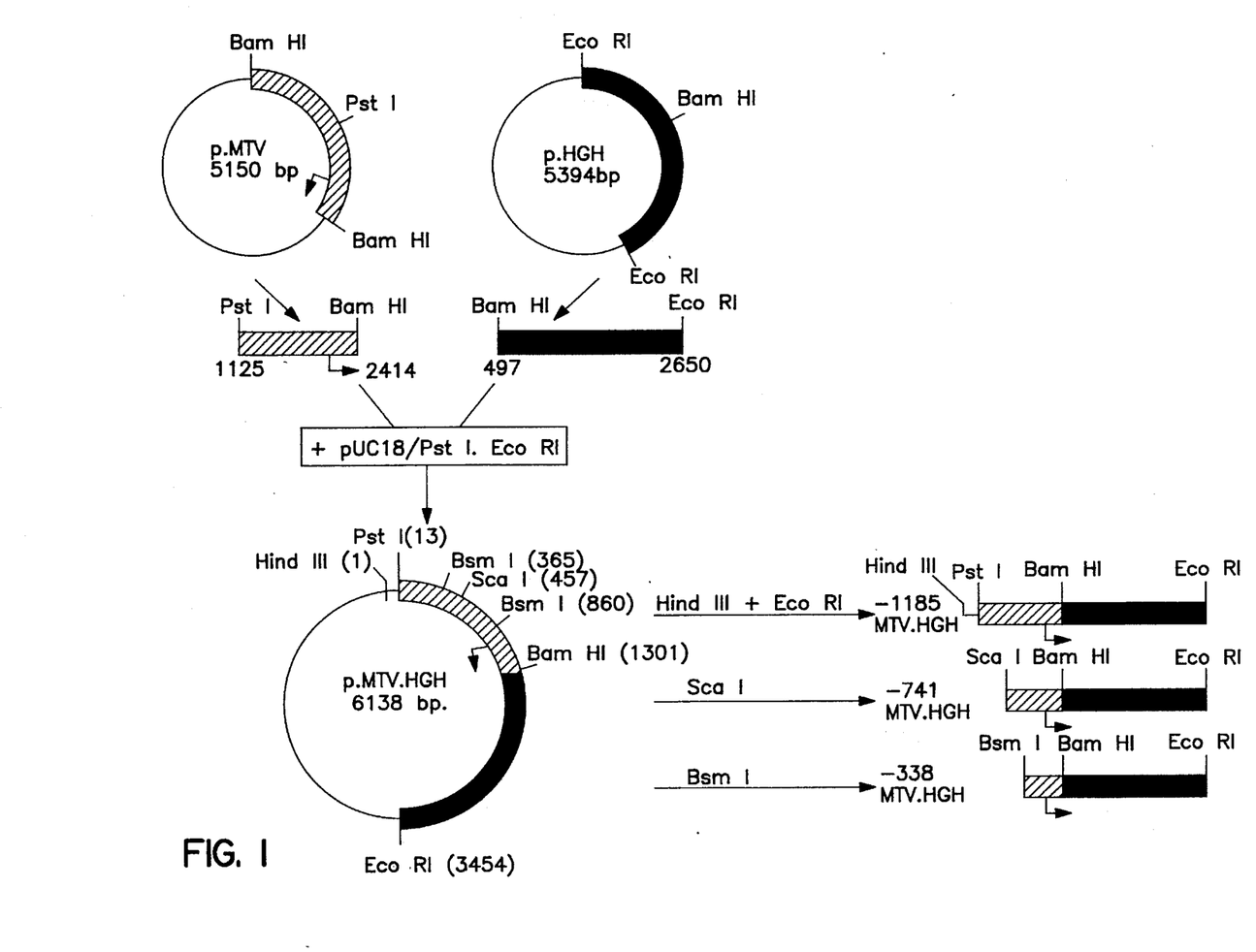
FIGS. 1–5 depict the construction of DNA inserts encoding hGH for embryo transfection in the generation of hGH transgenic animals.
Figure 2:
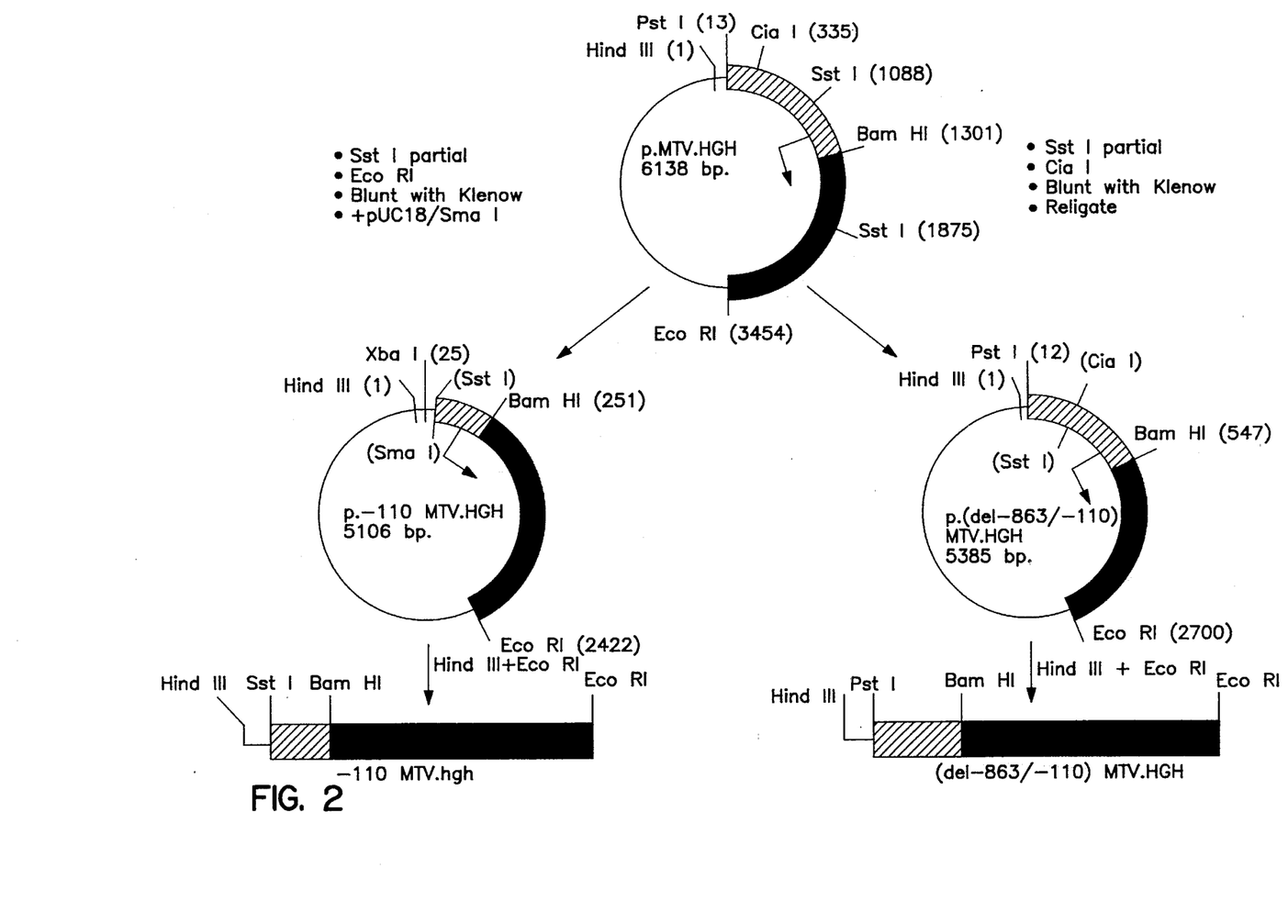

The MTV-hGH gene was constructed as follows and is diagrammed in FIG. 1. The gene for human growth hormone is widely available in nature or may be synthesized from known DNA sequence information. A 2153 base pair (bp) BamHI to EcoRI fragment containing the entire hGH protein coding region and its mRNA polyA addition sequence was purified on a low melt agarose gel. The MTV long terminal repeated sequence (LTR) was obtained from the PA9 plasmid described by Huang, A. L.; Ostrowski, M. C.; Bernard, O., Huger, G. L.; Cell 27:245–255 (1981), PA9 was digested by PstI and BamHi and the 1287 bp fragment containing the LTR purified from a low melt agarose gel. This fragment contains the regions responsible for controlling initiation of transcription and also contains the MTV RNA cap site. These two fragments were ligated into a pUG18 vector cut with PstI and EcoRI to generate a 6138 bp plasmid containing the hGH gene 3' to the MTV LTR (pMTV-hGH). This plasmid was digested with HindIII and EcoRI, and the 3454 bp fragment containing MTV-hGH purified from a low melt gel.

Five other MTV-promoted hGH fragments were made from pMTV-hGH.

(a) ScaI digestion of pMTV-hGH produced the 2997 bp fragment named "–741 MTV-hGH".

(b) BsMI digestion of pMTV-hGH produced the 2594 bp fragment named "–338 MTV-hGH".

(c) The p-110.MTV-hGH plasmid was made by carrying out a partial digestion of pMTV-hGH with SstI, then a complete digestion with EcoRI. The ends of the fragments were made blunt with Klenow polymerase, the 2366 bp fragment (from bases 1088 to 3454 in pMTV.hGH) purified and ligated into a SmaI cut pUG18 plasmid. The –110 MTV-hGH gene was purified after digestion of this plasmid with HindIII and ECoRI.

(d) The p (del –863/–110) MTV-hGH plasmid was produced from the pMTV-hGH plasmid by carrying out a partial digestion with SstI, a complete digestion with ClaI and purification of the 5385 bp fragment. The ends were made blunt with Klenow polymerase and the plasmid generated by self ligation. The del (–863/–110) MTV-hGH gene was purified from this plasmid after digestion with HindIII and EcoRI.

Figure 3:
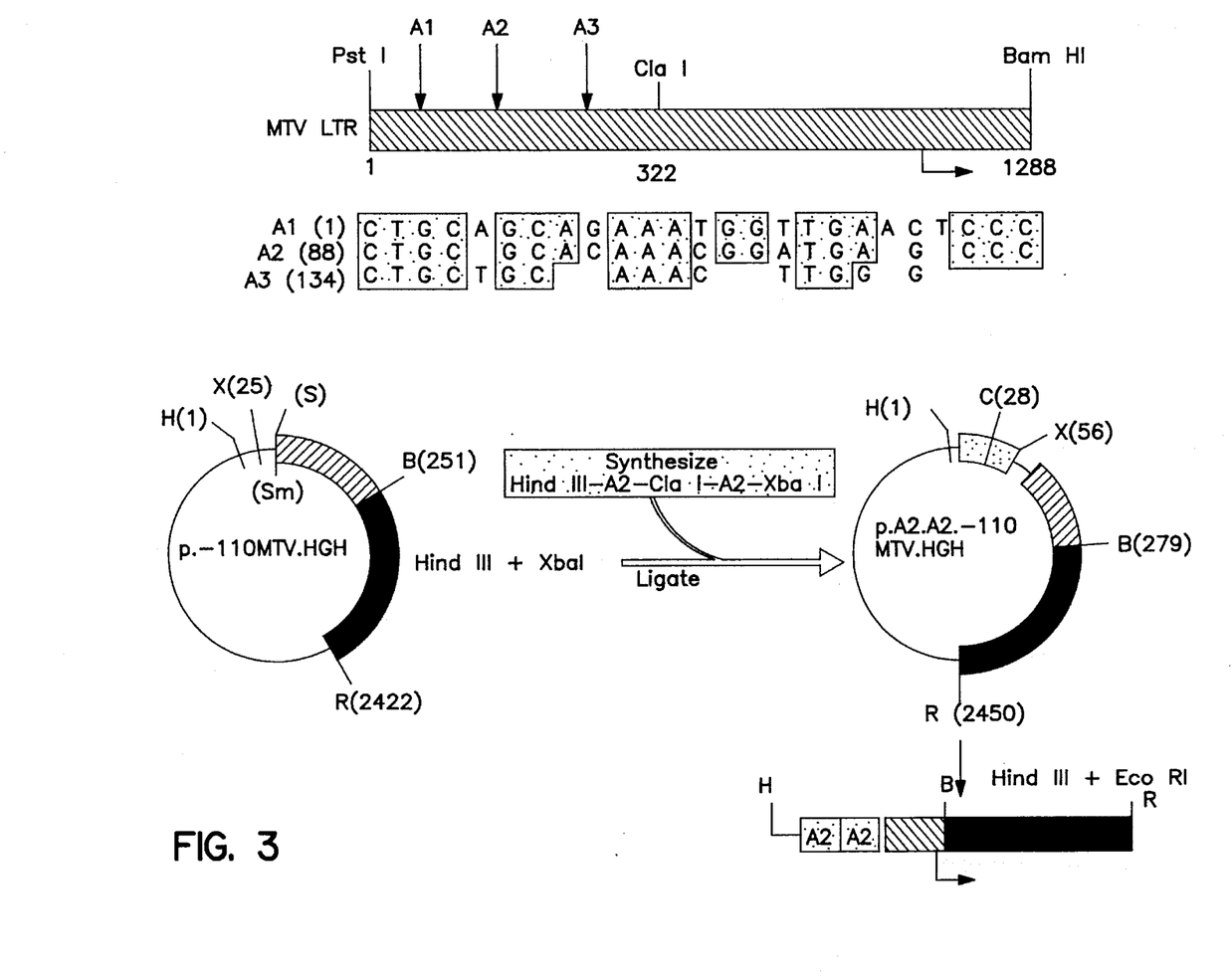
Figure 4:
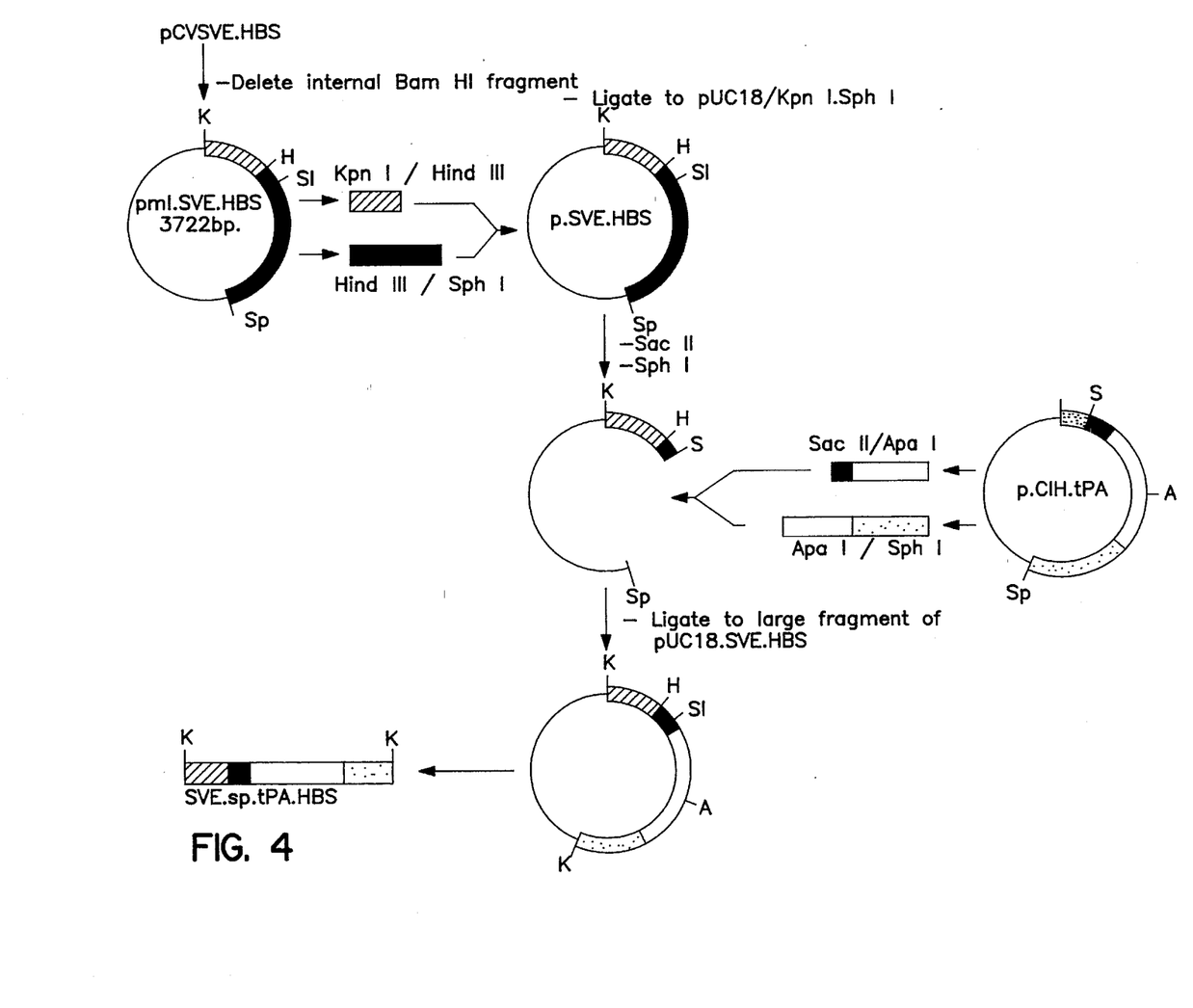
Figure 5:
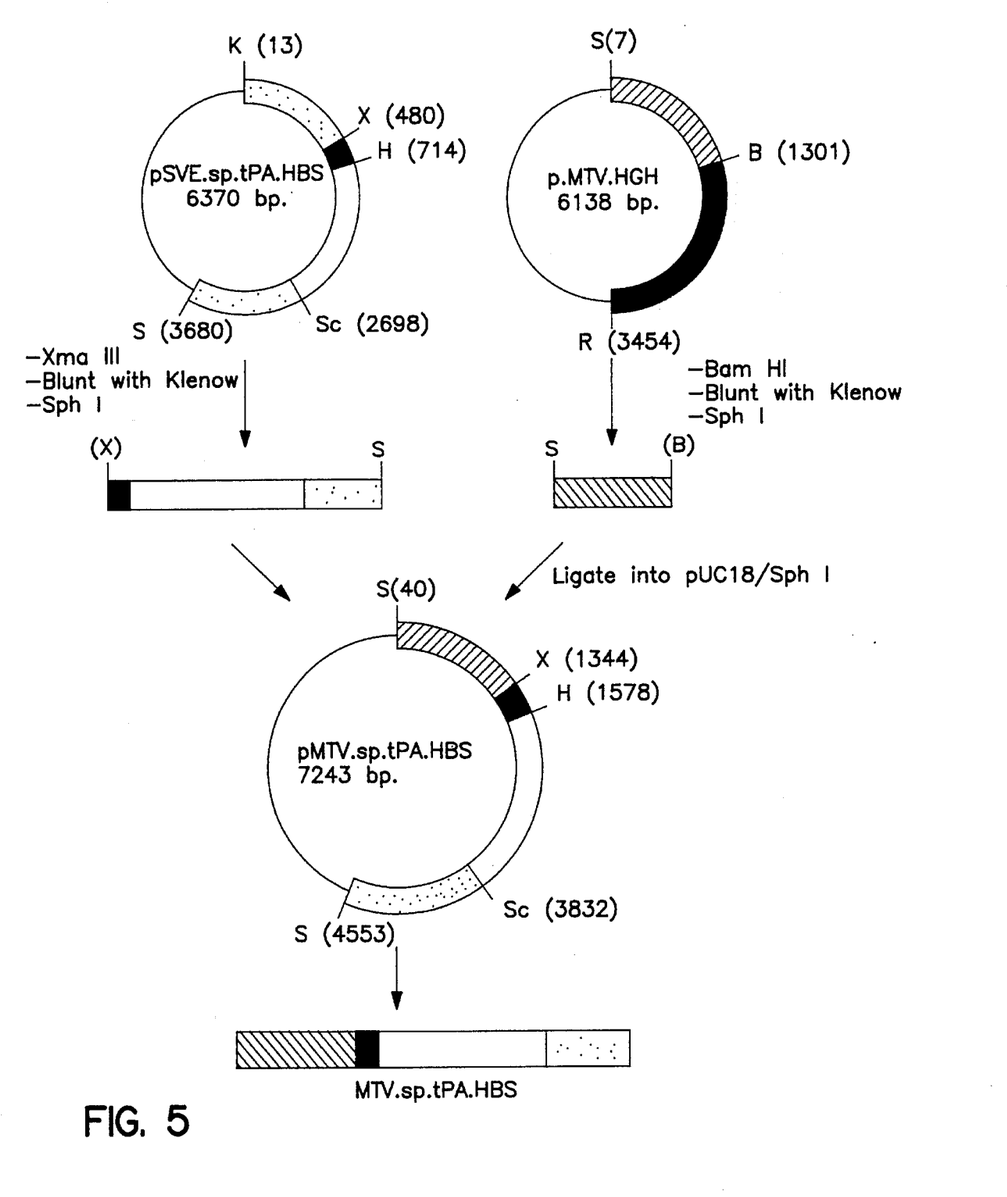

(e) The pA2.A2 –110 MTV-hGH plasmid was generated from the p-110 MTV-hGH plasmid: two complementary synthetic DNA oligonucleotides with the sequences i) 5'AGCTT(A2)ATCGAT(A2)T 3' ii) 3'A(A2)'TAGCTA(A2)'AGATC 5' were synthesized where A2 is shown in FIG. 3 and (A2)' is its complement. Note that one half of a HindIII site is located at the 5' end, one half of an XbaI site at the 3' end and a ClaI site separating the two A2 sequences. These two oligonucleotide sequences were annealed to each other to form a double stranded DNA (the A2.A2 oligonucleotide). The p-110 MTV-hGH was digested with HindIII and XbaI, the ends dephosphorylated with bacterial alkaline phosphatase and the synthetic annealed A2.A2 oligonucleotide ligated into this plasmid. Orientation and sequence were confirmed and the A2.A2 –110 MTV-hGH gene was purified from a HindIII and EcoRI digest of pA2.A2–110 MTV-hGH.

2. pSVE.tPA

The plasmid pSVE.tPA.tPA.HBS was prepared as described below. pML.SVE.HBS was generated from pSVSVE.HBS (EP 160,457) by deleting the internal BamHI fragment such that the plasmid has the SV40 early region 5' to the hepatitis surface antigen polyA addition site with a number of convenient cloning sites in between. The SVE-.HBS region was then shifted to pUG18 (Pharmacia) by ligating the KpnI to HindIII 376 bp fragment (SV40 early region) and the HindIII to SphI 812 bp fragment. (HBS poly A addition signal) into pUC18 that had been digested with KpnI and SphI to generate p.SVE.HBS This plasmid was digested with SacII and HindIII and the SacII to ApaI 1868 bp fragment and the ApaI to HindIII 1354 bp fragment from pCIHtPA plasmid ligated in to form pSVE.splice.tPA.HBS. The gene SVE.splice.tPA.HBS was purified from this plasmid after digestion with KDnI.

3. MTV-tpA

The plasmid p.MTV.splice.tPA.HBS (pMTV.tPA) was made by first purifying the following fragments: 1) the 1294 bp SphI to BamHI fragment (the BamHI was made blunt with Klenow polymerase prior to digestion with SphI); 2) the 3200 XmaIII (blunt with Klenow polymerase) to SphI fragment from the plasmid pCIH tPA (U.S. Ser. No. 907, 185): and 3) pUC18 cut with SphI and dephosphorylated with bacterial alkaline phosphatase. The tPA fragment from pCIHtPA contains, in 5' to 3' order, the splice donor from human cytomegalovirus (HCMV), the splice acceptor from the human immunoglobulin heavy chain locus, human tPA cDNA and the hepatitis polyA addition signal. These three fragments were ligated to form pMTV.splice.tPA.HBS. The gene MTV.splice.tPA.HBS was obtained by digesting pMTV.splice.tPA.HBS with SphI and recovering the 4513 bp fragment.

4. SVE.FVIII

The gene SVE.splice. FVIII.SV polyA was prepared from the plasmid pCIS FVIII (described in U.S. patent application Ser. No. 6/907,297) after digestion of the plasmid with AatII.

EXAMPLE 2

Generation of Transgenic Mice

The purified linear DNA molecules were injected into one pronucleus of one-cell fertilized mouse eggs. The eggs were derived from a mating between C57BL/65 females and CD-1 males in the case of the hGH transgenic mice, and CD-1 females and (C57BL/65xDBA/2)F1 males for the MTV-tPA, SVE-tPA and SVE-FVIII transgenic mice. The females were induced to ovulate by a standard protocol. Approximately sixty hours before mating, each female mouse received 5 units of pregnant mare serum; 48 hours later each female received 5 units of human chorionic gonadotropin and were individually caged with a male. Both males and females had food and water ad libitum and were maintained on a 12-hour light/12-hour dark cycle. Females that had mated (as indicated by the presence of a vaginal plug) were sacrificed, and fertilized eggs washed from the uterine tubules. This was accomplished by teasing open the ampullae of the tubules. The fertilized eggs were freed of the surrounding cumulus cells by a brief (1–5 minute) digestion with hyaluronidase and rinsed in five to ten changes of a standard balanced salt buffer.

The eggs were placed in a drop (approximately 100 µl) of this buffer in a depression slide and immediately covered with paraffin oil to prevent dehydration. This slide containing the eggs was placed on the stage of a Nikon microscope (inverted with Normarski optics). Each egg was in turn held securely by a holding pipette and DNA injected into one pronucleus. The holding pipette was fashioned on a David Kopf pipette puller and a De Fonbrune microforge from glass capillaries (World Precision Instruments, TW 100-F4) so that the tip was tapered from the full width of 1.2 mm to an external diameter of approximately 200 µM. This tip was fire-polished on the microforge so that the internal diameter was approximately 50 µM. This holding pipette was filled with buffer and connected via thick-walled tubing to a micrometer syringe. The connecting tubing and the micrometer tubing were filled with paraffin oil. This holding pipette was fitted onto the left unit of a Leitz micromanipulator and the tip lowered into the drop containing the eggs. By manipulating the syringe, a slight negative pressure can be created at the tip of the holding pipette, which will keep the egg to be injected securely fixed to the end of the holding pipette. The injection pipette was fashioned from the same glass tubing (as the holding pipette) and fashioned on the same David Kopf pipette puller. In this case the external diameter at the tip of the pipette is approximately 1 µM. This injection pipette is fitted to the right Leitz manipulator and is connected via plastic tubing to the regulator on a cylinder of compressed air. The tip of the injection pipette is lowered into the drop containing the eggs and DNA is forced out of the tip by turning on the compressed air. The DNA is injected into the pronucleus of the egg by moving the tip of the injection pipette into the pronucleus of the egg. That the DNA is being introduced into the pronucleus can be seen by the fact that the pronucleus swells. When the pronucleus has increased in diameter by 10–25 percent, the pipette tip is withdrawn and all other eggs in the drop similarly injected.

The injected eggs are then transferred to a pseudopregnant female mouse for development to birth. The pseudopregnant females are prepared by mating CD-1 females (Charles River Laboratories) to CD-1 males that have been vasectomized. These matings occur during the same night as the matings between the fertile pairs used for collecting eggs. This ensures that the recipient female has the appropriate hormonal status to accept the injected one-cell fertilized eggs. The eggs are transferred to the recipient female by a surgical procedure. The female is anesthetized, an incision is made through the skin and the body wall, and the uterine tubules are exposed. A small incision is made in the ovarian sac and the injected eggs transferred to the proximal end of the uterine tubules via the infundibulum. The body wall is then sutured and the skin closed with skin clips. Approximately nineteen days later, pups derived from the injected eggs are born; these are weaned from the mother when they are four weeks old.

The identification of the transgenic mice is made by Southern blot analysis of tail DNA. When the mice are weaned, approximately 0.5 cm of tail is removed and DNA purified from the tail. A digestion mix (400 HI of a solution containing 50 mM Tris (pH 7.4), 100 mM NAG1, 1 mM EDTA, 0.5% SDS, and 100 µg/ml proteinase K) is added to the tail in an Eppendorf tube and the tube shaken overnight at 65° C. The following morning 75 µl of 8M potassium acetate is added, the tubes are chilled for 30–60' (4° C.) and then 500 µl chloroform is added. The contents of the tubes are thoroughly mixed, then centrifuged in a Savant or Eppendorf microfuge for 10'. The upper aqueous layer is removed to a new tube and an equal volume of ethanol at room temperature is added. The contents are mixed and the precipitated DNA is pelleted by centrifuging the tubes for 2'. The pellet is rinsed in 70 percent ethanol in water, allowed to dry, and then resuspended in 400 µl of TE (10 mM Tris, 1 mM EDTA pH 7.4). Approximately 10 µl of this tail DNA is digested with appropriate endonuclease restriction enzymes and the cleaved DNA fragments separated by electrophoresis through an 0.8 percent gel. The DNA is denatured in situ using 0.5 M NaDH and 1.5 M NaCl neutralized with 1.5 M NaCl and 1.0 M Tris, pH 7.5, and transferred to nitrocellulose sheets using conventional "Southern" procedures. The DNA is covalently attached to the nitrocellulose by baking at 80° C. in a vacuum. These nitrocellulose sheets are hybridized overnight to a DNA probe labeled with $^{32}P$ by primer extension. Following this overnight hybridization, excess nonbound radioactive probe is washed from the sheets and the filter exposed on X-ray sensitive film. Under the conditions used (hGH probe and high hybridization stringency), DNA from normal wild type mice do not reveal any bands by this Southern blotting procedure; transgenic mice, in contrast, will have one or more detectable bands. In one original experiment, using the −741 MTV hGH gene, 170 eggs were transferred; 29 mice were born, 29 were analyzed, and 2 were transgenic. One of these mice (a male, no. 249-2) was mated to a nontransgenic littermate. Transgenic offspring were identified by Southern blotting as described above. This line of mice (referred to as the 249-2 family) was bred for a further two generations by crossing to CD-1 mice.

The level of hGH protein in the serum of these mice was determined by a commercially available competitive-type radioimmunoassay. The level of hGH in the serum of transgenic males was approximately 150–200 ng/ml and in the females 50–100 ng/ml. All mice in the 249-2 family identified as transgenic by Southern Blotting had comparable hGH serum levels. A summary of the data accumulated in the hGH studies reported here is set forth below in Table 2.

TABLE 2

| Gene | # eggs trans-ferred | # mice born | Tr. mice born | Tr. mouse name | | Sp | Ki | Li | Th | Sg | Br | Te | He | Lu | Pg | Sv | Pa | Ut |
|---|---|---|---|---|---|---|---|---|---|---|---|---|---|---|---|---|---|---|
| | | | | | | | | | | | RNA* | | | | | | | |
| MTVHGH | 150 | 12 | 4 | 247-4 | F | ++ | + | o | + | + | + | | | | | | | |
| | | | | 247-6 | M | + | + | o | + | ++ | + | ++ | | | | | | |
| | | | | 247-7 | M | + | + | o | o | + | + | + | | | | | | |
| | | | | 247-8 | F | + | + | o | + | ++ | + | | | | | | | |
| -741 MTVHGH | 170 | 29 | 2 | 249-2 | M | + | + | | | | | | | | | | | |
| | | | | 249-2-9 | M | + | + | o | + | + | + | ++ | + | ++ | + | o | o | |
| | | | | 249-6 | F | o | o | o | o | o | o | | | | | | | o |
| -338 MTVHGH | 240 | 26 | 3 | 248-1 | M | o | o | o | o | o | o | + | | | | | | |
| | | | | 248-14 | F | o | + | o | o | o | + | | | | | | | o |
| | | | | 248-22 | M | o | o | o | o | o | + | + | | | | | | |
| | | | | 248-22-15 | F | o | o | o | o | o | + | | o | + | | | o | o |
| -110 MTVHGH | 324 | 39 | 3 | 257-15 | M | o | o | o | o | o | o | o | | | | | | |
| | | | | 340-5 | | | | | | | | | | | | | | |
| | | | | 340-5-1 | M | o | o | o | o | o | o | + | | | | | | |
| | | | | 340-10 | F | o | o | o | o | o | + | | o | o | | | o | o |
| del(863/110)MTVHGH | 229 | 29 | 7 | 275-3 | M | + | ++ | + | + | ++ | + | ++ | | | | | | |
| | | | | 275-12 | F | o | + | o | + | ++ | + | | + | ++ | | | o | + |
| | | | | 275-14 | M | | | | | | | | | | | | | |
| | | | | 275-14-4 | M | + | o | o | + | ++ | + | ++ | + | ++ | + | | | |
| | | | | 275-18 | F | + | ++ | + | + | + | ++ | | | | | | | |
| | | | | 276-1 | M | o | + | + | + | ++ | + | + | | | | | | |
| | | | | 276-3 | | | | | | | | | | | | | | |
| | | | | 278-4 | F | + | + | o | + | ++ | + | | + | ++ | | | o | + |
| A2.A2-110MTVHGH | 197 | 29 | 3 | 352-10 | | | | | | | | | | | | | | |
| | | | | 352-10-2 | M | o | o | o | o | o | ++ | o | o | o | o | o | o | |
| | | | | 352-11 | F | o | o | o | o | o | ++ | | o | o | | | o | o |
| | | | | 355-1 | | | | | | | | | | | | | | |

| Gene | # eggs transferred | # mice born | Tr. mice born | Tr. mouse name | Ov | Sm | Ta | Serum protein | Transmission | Tolerant |
|---|---|---|---|---|---|---|---|---|---|---|
| | | | | | | RNA* | | | | |
| MTVHGH | 150 | 12 | 4 | 247-4 | | | | >2000 | | |
| | | | | 247-6 | | | | 400 | | |
| | | | | 247-7 | | | | 15 | | |
| | | | | 247-8 | | | | 400 | | |
| -741 MTVHGH | 170 | 29 | 2 | 249-2 | | | | | | |
| | | | | 249-2-9 | | | | 200 | yes | yes |
| | | | | 249-6 | o | | | | | |
| -338 MTVHGH | 240 | 26 | 3 | | | | | | | |
| | | | | 248-14 | o | | | | | |
| | | | | 248-22 | | | | | yes | |
| | | | | 248-22-15 | o | o | o | >3 | | |
| -110 MTVHGH | 324 | 39 | 3 | 257-15 | | | | | | |
| | | | | 340-5 | | | | | yes | |
| | | | | 340-5-1 | | | | >3 | | |
| | | | | 340-10 | o | o | | >3 | no | |
| del(863110)MTVHGH | 229 | 29 | 7 | 275-3 | | | | >500 | | |
| | | | | 275-12 | + | ++ | | 60 | no | |
| | | | | 275-14 | | | | | | |
| | | | | 275-14-4 | | o | + | 30 | yes | yes |
| | | | | 275-18 | | | | 400 | | |
| | | | | 276-1 | | | | >500 | | |
| | | | | 276-3 | | | | >400 | | |
| | | | | 278-4 | + | + | | | no | |
| A2.A2-110MTVHGH | 197 | 29 | 3 | | | | | | | |
| | | | | 352-10-2 | | | | >4 | yes | |
| | | | | 352-11 | o | o | | >4 | no | |
| | | | | 355-1 | | | | >4 | yes | |

*Sp, spleen; Ki, kidney; Li, liver; Th, thymus; Sg, salivary gland; Br, brain; Te, testes; He, heart; Lu, lung; Pg, preputial gland; Sv, seminal vesicles; Pa, pancreas; Ut, uterus; Ov, ovaries; Sm, skeletal muscle; Ta, tail.

The immune response to hGH in these transgenic mice and their nontransgenic littermates was assessed as follows: Each mouse was injected (subcutaneously) with 5 μg of mature hGH from an E. coli transformant which secreted mature hGH into the periplasm, in 0.1 ml 5mM PBS three times per week (Monday, Wednesday, Friday) for eight weeks. The mice were bled prior to the first, seventh, tenth, and sixteenth injection, and one day following the twenty-fourth injection. Serum was prepared from the blood samples and the level of hGH and antibodies to hGH determined. Included in this study, as further negative controls, were a group of unrelated non-hGH transgenic mice with similar outbred genetic backgrounds.

Tolerance and the antibody response to the hGH preparations was measured by radioimmunoprecipitation (RIP). The assay contains radiolabeled tracer (125I-met-hGH) to which the iodine is covalently coupled by the chloramine T technique (Hunter, W. M. [1978] in *Handbook of Experimental Immunology*, Weir, D. M., ed., 3rd ed., Chapter 14, Blackwell Scientific Publications, Oxford, England). To perform the assay 0.1 mL of $^{125}$I-met-hGH (20,000 cpm) in phosphate buffered saline (0.14 M NaCl, 0.003 M KCL, 0.016 M phosphate pH 7.2–7.4) containing 0.5 percent bovine serum albumin and 0.01 percent Thimerosal PBSAT was added to 0.1 mL of various dilutions of the test sera. The serum dilutions are performed with normal horse serum beginning at a 1:5 dilution (final dilution of 1:10 in assay) and proceeding in a step wise manner with 3 fold dilutions. The mixture is incubated for 12–24 hours at ambient temperature. 0.8 ml of 15.6 percent polyethylene glycol 8000 containing 0.1% Thimerosal was added and the mixture was incubated an additional 30 minutes at ambient temperature. The tubes are centrifuged for 20 minutes at 2000 xg. The pellet was resuspended in 12.5 percent PEG 8000 containing 0.01 percent Thimerosal, incubated 15 minutes at ambient temperature and centrifuged for 20 minutes at 2000 xg. The supernatant was decanted and the tube containing the pellet counted in a gamma counter. Any serum that resulted in counts that were 2-fold higher than background was considered to be positive. The antibody titer can be calculated as the reciprocal of the serum dilution that immuno-precipitates 20 percent of the maximum cpm immunoprecipitated by a positive control serum from an immunized non-transgenic mouse or a transgenic mouse expressing a protein unrelated to the test protein.

The results show that five of six control non-hGH transgenic males made high levels of hGH antibodies and all five control females made hGH antibodies after exposure to the mature hGH preparation. The reason for the one male failing to make antibodies is not known. In contrast, none of the transgenic mice (four males and three females) had detectable hGH antibodies after injection with the mature hGH preparation. Transgenic animals producing the highest levels of serum hGH also were tolerant to methionyl N-terminal hGH.

Eight transgenic mice that contain in their genome the SVE-FVIII gene, nine transcribing the MTV-tPA gene, and six transcribing the SVE-tPA gene were generated from fertilized eggs using a protocol which was identical to that used in the hGH gene transfections except that the matings used to derive the eggs to be injected were CD-1 females crossed with C57BL/6JxDBA/2 males. In these three cases the Southern blot analysis for the presence of the transfected gene used a different restriction enzyme and a different probe.

I claim:

1. A method for determining the immunogenicity of a potentially immunogenic polypeptide in a mouse which comprises:

(a) providing a transgenic mouse whose somatic and germ cells contain a DNA sequence encoding a heterologous polypeptide, said DNA sequences having been introduced into said mouse or an ancestor of said mouse during an embryonic stage and said DNA sequence being transcribed and continuously expressed under the control of a promoter, whereby said mouse becomes immunologically tolerant to said heterologous polypeptide as a result of the expression of said DNA sequence;

(b) administering to said mouse of step (a) said potentially immunogenic polypeptide, wherein the potentially immunogenic polypeptide is a variant of said heterologous polypeptide; and (c) determining the presence of antibodies specific for said potentially immunogenic polypeptide using radio-immunoassays or ELISA systems as an indication of the immunogenicity of said potentially immunogenic polypeptide.

2. The method of claim 1 wherein said potentially immunogenic polypeptide is undenatured.

3. The method according to claim 2 wherein said potentially immunogenic polypeptide is produced in recombinant cell culture from cells transformed with nucleic acid encoding the heterologous polypeptide.

4. The method of claim 1 wherein the heterologous polypeptide is a human polypeptide.

5. The method according to claim 3 wherein said potentially immunogenic polypeptide is an amino acid sequence variant of said heterologous polypeptide.

6. The method according to claim 1 wherein said potentially immunogenic polypeptide is an amino acid sequence variant of said heterologous polypeptide.

7. The method according to claim 1 wherein said potentially immunogenic polypeptide is a conformational variant of said heterologous polypeptide.

8. The method according to claim 1 wherein said potentially immunogenic polypeptide is an interspecies variant of the heterologous polypeptide.

9. The method according to claim 1 wherein said potentially immunogenic polypeptide is a chemically modified variant of the heterologous polypeptide.

* * * * *